United States Patent
Zimmerman et al.

(10) Patent No.: US 6,759,033 B2
(45) Date of Patent: Jul. 6, 2004

(54) METHOD FOR SLOWING THE DECOMPOSITION OF A COSMETIC COMPOSITION

(75) Inventors: Amy C. Zimmerman, Grand Rapids, MI (US); Ruth Elaine Harris, Belmont, MI (US)

(73) Assignee: Access Business Group International LLC, Ada, MI (US)

( * ) Notice: Subject to any disclaimer, the term of this patent is extended or adjusted under 35 U.S.C. 154(b) by 131 days.

(21) Appl. No.: 10/046,415

(22) Filed: Oct. 25, 2001

(65) Prior Publication Data

US 2002/0141955 A1 Oct. 3, 2002

Related U.S. Application Data

(62) Division of application No. 09/599,235, filed on Jun. 22, 2000, now abandoned.

(51) Int. Cl.[7] .............................. A61K 7/00; A61K 7/06; A61K 7/035; A61K 7/135
(52) U.S. Cl. .............................. 424/69; 424/59; 424/62; 424/70.1; 424/78.03; 424/401
(58) Field of Search .............................. 424/69, 59, 62, 424/401, 70.1, 78.03

(56) References Cited

U.S. PATENT DOCUMENTS

| | | |
|---|---|---|
| 5,078,989 A | 1/1992 | Ando et al. |
| 5,139,782 A | 8/1992 | Jung |
| 5,766,575 A | 6/1998 | Crotty et al. |
| 5,807,561 A | 9/1998 | Guerrero |
| 5,853,705 A | 12/1998 | Nakayama et al. |
| 6,071,525 A * | 6/2000 | Kim et al. ................... 424/62 |

FOREIGN PATENT DOCUMENTS

| | | |
|---|---|---|
| WO | WO98/22075 | 5/1998 |
| WO | WO99/56720 | 11/1999 |

* cited by examiner

*Primary Examiner*—Herbert J. Lilling
(74) *Attorney, Agent, or Firm*—Brinks Hofer Gilson & Lione; G. Peter Nichols

(57) ABSTRACT

A cosmetic composition includes a carrier, a skin-whitening agent, and sodium magnesium silicate. The sodium magnesium silicate is present in an amount effective to slow decomposition of the composition. A method of slowing the decomposition of a cosmetic composition containing a skin-whitening agent includes adding an effective amount of a sodium magnesium silicate to the composition.

8 Claims, No Drawings

METHOD FOR SLOWING THE DECOMPOSITION OF A COSMETIC COMPOSITION

This is a division of application Ser. No. 09/599,235 filed Jun. 22, 2000 now abandoned.

BACKGROUND OF THE INVENTION

The present invention relates to a cosmetic composition for external use containing a carrier, a skin-whitening agent, and sodium magnesium silicate.

Certain skin-whitening agents in cosmetic compositions oxidize over time, causing the cosmetic composition to decompose. The decomposition causes the cosmetic composition to darken and to develop an intense, undesirable odor. Certain skin-whitening ingredients are known to be worse than others for premature oxidation. For example, magnesium ascorbyl phosphate and botanical whiteners such as bearberry extract and others have been especially prone to premature oxidation. For this reason, cosmetic compositions containing these whitening agents tend to decompose, turn brown, and develop a foul odor. As a result, cosmetic compositions containing certain skin-whitening agents have very limited shelf lives.

Nevertheless, skin-whitening compositions are still in high demand, especially in Asian markets. For this reason, a method is needed to slow the decomposition of skin-whitening compositions and the resulting darkening and foul odor of the skin-whitening compositions. Surprisingly, adding sodium magnesium silicate to skin-whitening compositions dramatically slows the darkening of these compositions as well as the development of the undesirable odor. Accordingly, cosmetic compositions that contain skin-whitening agents susceptible to oxidation have longer shelf lives if those cosmetic compositions also contain sodium magnesium silicate.

SUMMARY OF THE INVENTION

In one aspect of the invention, a composition for topical use that has a melanin synthesis-inhibiting activity is provided. The composition comprises a carrier, a skin-whitening agent, and sodium magnesium silicate, wherein the sodium magnesium silicate is present in an amount effective to slow decomposition of the composition.

In another aspect of the invention, an improvement in a skin-whitening composition comprises an effective amount of sodium magnesium silicate to slow the decomposition of the composition.

In still another aspect of the invention, a method of slowing the decomposition of a cosmetic composition containing a skin-whitening agent comprises adding an effective amount of a sodium magnesium silicate to the composition.

It is noted that, unless otherwise stated, all percentages given in this specification and the appended claims refer to percentages by weight.

The present invention provides the foregoing and other features, and the advantages of the invention will become further apparent from the following detailed description of the presently preferred embodiments. The detailed description is merely illustrative of the invention and does not limit the scope of the invention, which is defined by the appended claims and equivalents thereof.

DETAILED DESCRIPTION OF THE PREFERRED EMBODIMENTS

In accordance with the present invention, a skin-whitening cosmetic composition is provided that comprises a carrier, a skin-whitening agent, and sodium magnesium silicate. The present invention also concerns preventing the premature oxidation of skin-whitening agents in cosmetic compositions, which causes the compositions to brown and to develop an odor over time.

Certain skin-whitening agents are especially prone to premature oxidation. These skin-whitening agents include, but are not limited to, magnesium ascorbyl phosphate and botanical extracts such as bearberry extract, lemon extract, cucumber extract, mulberry extract, licorice extract.

The cosmetic composition may contain other skin-whitening agents, whether or not those agents are prone to premature oxidation. Such skin-whitening agents may include all the known whitening agents and those that may be developed in the future. Although it is not possible to identify and list all known skin-whitening agents, the following skin-whitening agents may be included in the cosmetic composition of the present invention: tyrosinase inhibitors, free radical scavengers, chelating agents, and mixtures thereof.

Some tyrosinase inhibitors include, but are not limited to, arbutin, bearberry extract, orange extract, lemon extract, cucumber extract, mercaptosuccinic acid, mercaptodextran, kojic acid, derivatives of kojic acid, vitamin C, derivatives of vitamin C, hydroquinone and derivatives of hydroquinone, glutathione, cysteine and its derivatives such as N-acetyl-L-cysteine and those described in U.S. Pat. No. 5,296,500, the relevant portions of which are incorporated herein by reference, mulberry extract and its derivatives, licorice extract and its derivatives, rosemary extract and its derivatives, and mixtures thereof.

The kojic acid or its esters are represented by the formula:

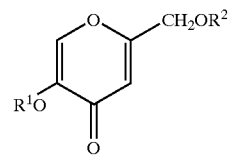

wherein $R^1$ and $R^2$ are the same or different, and each is hydrogen atom or an acyl group of 3 to 20 carbon atoms.

Non-exclusive examples of the esters are, for instance, kojic acid monoesters such as kojic acid monobutyrate, kojic acid monocaprate, kojic acid monopalmitate, kojic acid monostearate, kojic acid monocinnamoate and kojic acid monobenzoate; kojic acid diesters such as kojic acid dibutyrate, kojic acid dipalmitate, kojic acid distearate and kojic acid dioleate. A preferred monoester is an ester in which an OH group at 5-position of kojic acid is esterified. Esterification can improve stabilities against pH or sun light, while maintaining a melanin synthesis-inhibiting activity equal to that of kojic acid.

The free radical scavengers may include, but are not limited to ascorbic acid (vitamin C) and its derivatives, vitamin E, superoxide dismutase, acerola cherry extracts, acerola cherry fermentates The vitamin C and its derivatives may be present in any isomeric form. For example, they can all be in cis configurations, they can all be in trans configurations, or they can be in a mixture of cis and trans configurations.

Non-exclusive examples of the vitamin C derivatives are, for instance, the alkyl esters of L-ascorbic acid where the alkyl portion has from 8 to 20 carbon atoms. For example, such esters include, but are not limited to L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate, tetrahexyl decyl ascorbate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; their salts with alkaline earth metals such as calcium and magnesium. A preferred whitener is magnesium ascorbyl phosphate. The vitamin C derivatives can be used alone or in a mixture of two or more.

Other skin-whitening agents may include gingko extract, carob extract, rose fruit extract, geranium herb extract, Perilla extract, cinnamon extract, sweet marjoram extract, Arnica extract, Concha Blanca extract, cola ed Caballo, Piri-Piri, Pinon Negro, Pinon Blanco, extracts of clove, alfalfa, Baliospermum montanum, Melia azadirachta, convolvulus arvensis, Gaiyo, Sansonin, Syuroyo, Seimkko, Soukyo, Taiso, Hakusempi, Woodfordia fructosa, Lagerstroemia speciosa, passiflorine, tepezcohite, amoule, Hobiyu, Baffalo Uri, Achote, Guayule, Adhatoda, Cymbopogon nardus, Desmodium gangeticum, Murraya koenigii, Smilax zeylanica, Gastrodia elata, Karukeija, Biota orientalis, Kichiascoporia, Arecatachu, Phyllostachys Nigra leaves, Atractylodes japonica, Koidzumi, Tila, Camotede Azafran, Jamaica, Poleo verde, Navo negro, Cyperus, Kanzo, Broussonetia, Karojitsu, Trichosanthis Radix, Dioscorea Phizoma, and Aquilliaria.

Other skin-whitening agents may include teprenone, dihydroxy-isoquinoline, indomethacin, 3-hydroxymanule, vitamin K (such as vitamin K1–K7, its homologues, salts, and derivatives), thiazolidinone derivatives, and kynurenine and its derivatives and salts.

The skin-whitening agent may be used in the cosmetic composition of the present invention in an amount of from about 0.001% to about 99%. Preferably, the skin-whitening agent is present in the composition in an amount of from about 0.01% to about 20%. More preferably, the amount ranges from about 0.1% to about 10%.

Sodium magnesium silicate is commercially available under the trade name LAPONITE. It is a synthetic silicate clay with a composition mainly of magnesium and sodium silicate.

Surprisingly, sodium magnesium silicate has the unexpected and beneficial effect of reducing the time and temperature-induced darkening effect of the skin-whitening agent in the cosmetic composition. In other words, sodium magnesium silicate prevents the premature darkening of the cosmetic composition. The results are especially impressive when the cosmetic composition includes skin-whitening agents prone to oxidation such as magnesium ascorbyl phosphate and botanical extracts.

Surprisingly, sodium magnesium silicate also improves the odor of the composition by reducing the time and temperature-induced development of foul odors as the skin-whitening agents oxidize. In other words, sodium magnesium silicate prevents the premature development of a foul odor. The results are especially impressive when the cosmetic composition includes skin-whitening agents prone to oxidation such as magnesium ascorbyl phosphate and botanical extracts.

Sodium magnesium silicate may be used in the whitening composition in an amount from about 0.001% to about 99%. Preferably, sodium magnesium silicate is present in the composition in an amount of from about 0.01% to about 10%. More preferably, the amount ranges from about 0.1% to about 5%.

The cosmetic compositions of the present invention may be prepared in various forms. For example, they may be in the form of a cosmetic preparation such as an emulsion, liniment or ointment lotions, creams, (both oil-in-water, water-in-oil, and multiple phase), solutions, suspensions (anhydrous and water based), anhydrous products (both oil and glycol based), gels, sticks, surfactant systems (cleansers, shampoos, facial washes, etc.), powders, masks, pack or powder, or the like.

The cosmetic compositions of the present invention generally include a cosmetically acceptable or pharmaceutically acceptable carrier. The terms "pharmaceutically acceptable" and "cosmetically acceptable" means those drugs, medicaments, or inert ingredients which are suitable for use in contact with the tissues of humans and lower animals without undue toxicity, incompatibility, instability, irritation, and the like, commensurate with a reasonable benefit/risk ratio.

The carrier usually forms from about 1% to about 99.9%, preferably from about 50% to about 99% by weight of the composition, and can, in the absence of other cosmetic adjuncts, form the balance of the composition.

Other optional ingredients can be included in the cosmetic composition of the present invention. As a non-limiting illustration, the optional ingredients can include UV absorbers, fragrances, preservatives, thickeners, ph adjusters, etc, so long as they do not interfere with the function of the skin-whitening agent and the sodium magnesium silicate.

EXAMPLES

Following are examples of compositions made according to the present invention. The examples are merely illustrative; they are not limiting.

Each example was compared with a "control" cosmetic composition that had all the same ingredients as the example except for sodium magnesium silicate. The cosmetic composition of each example was then qualitatively compared to its control cosmetic composition after exposure to the same conditions.

Example 1

| Ingredient | Weight Percent |
| --- | --- |
| Laponite XLG (Sodium Magnesium Silicate) | 0.50 |
| Magnesium Ascorbyl Phosphate | 3.00 |
| Botanical whitening complex | 1.00 |
| Water and Optional Ingredients | q.s. |

The composition of Example 1 was qualitatively compared to its control composition after 30 days at 50° C. The control composition decomposed, changed its color to brown, and began developing a foul odor, as expected. Surprisingly, the composition of Example 1 maintained its pleasant odor and appearance.

Example 2

| Ingredient | Weight Percent |
| --- | --- |
| Laponite XLG (Sodium Magnesium Silicate) | 1.00 |

-continued

| Ingredient | Weight Percent |
| --- | --- |
| Bearberry Extract | 2.00 |
| Lactic Acid | 2.00 |
| Acerola Fermentate | 3.00 |
| Water and Optional Ingredients | q.s. |

The composition of Example 2 was qualitatively compared to its control composition after 30 days at 50° C. The control composition decomposed, changed its color to brown, and began developing a foul odor, as expected. Surprisingly, the composition of Example 2 maintained its pleasant odor and appearance.

Example 3

| Ingredient | Weight Percent |
| --- | --- |
| Laponite XLG (Sodium Magnesium Silicate) | 1.00 |
| Magnesium Ascorbyl Phosphate | 3.00 |
| Vitamin E | 0.05 |
| Water and Optional Ingredients | q.s. |

The composition of Example 3 was qualitatively compared to its control composition after 30 days at 50° C. The control composition decomposed, changed its color to brown, and began developing a foul odor, as expected. Surprisingly, the composition of Example 3 maintained its pleasant odor and appearance.

Based on the above results, the addition of magnesium ascorbyl phosphate to a cosmetic composition containing a skin-whitening agent prone to premature oxidation will extend the shelf life of that cosmetic composition. Magnesium ascorbyl phosphate may extend the shelf life of the cosmetic by as much as 25%, preferably by as much as 50%, more preferably by as much as 100%, or most preferably by as much as 200%.

It should be understood that a wide range of changes and modifications could be made to the embodiments described above. It is therefore intended that the foregoing description illustrates rather than limits this invention, and that it is the following claims, including all equivalents, which define this invention.

What is claimed:

1. A method of slowing the decomposition of a cosmetic composition containing a skin-whitening agent, the method comprising adding an effective amount of a sodium magnesium silicate to the composition.

2. The method of claim 1 wherein the composition comprises from about 0.001% to about 99% by weight of a skin-whitening agent.

3. The method of claim 1 wherein the composition comprises from about 0.01% to about 10% by weight of the sodium magnesium silicate.

4. The method of claim 1 wherein the skin-whitening agent is selected from the group consisting of tyrosinase inhibitors, free radical scavengers, chelating agents and mixtures thereof.

5. The method of claim 4 wherein the tyrosinase inhibitors are selected from the group consisting of arbutin, bearberry extract, lemon extract, cucumber extract, mercaptosuccinic acid, mercaptodextran, kojic acid, derivatives of kojic acid, vitamin C, derivatives of vitamin C, hydroquinone, glutathione, cysteine, mulberry extract, licorice extract and its derivatives, and mixtures thereof.

6. The method of claim 1 wherein the skin-whitening agent is selected from the group consisting of bearberry extract, lactic acid, acerola fermentate, magnesium ascorbyl phosphate, and mixtures thereof.

7. The method of claim 1 wherein the sodium magnesium silicate is present in an amount effective to prevent premature darkening of the cosmetic composition and to prevent premature development of a foul odor.

8. The method of claim 7 wherein the composition comprises from about 0.001% to about 99% by weight of the sodium magnesium silicate.

* * * * *